(12) United States Patent
van den Brink et al.

(10) Patent No.: US 7,776,581 B2
(45) Date of Patent: Aug. 17, 2010

(54) METHOD OF PRODUCING AN ASPARTIC PROTEASE IN A RECOMBINANT HOST ORGANISM

(75) Inventors: Johannes M. van den Brink, Herlev (DK); Marianne K. Harboe, Lyngby (DK); Steen G. Petersen, Rodovre (DK); Henrik Rahbek-Nielsen, Birkered (DK)

(73) Assignee: Chr. Hansen A/S, Horsholm (DK)

( * ) Notice: Subject to any disclaimer, the term of this patent is extended or adjusted under 35 U.S.C. 154(b) by 854 days.

(21) Appl. No.: 10/518,414

(22) PCT Filed: Jun. 16, 2003

(86) PCT No.: PCT/DK03/00398

§ 371 (c)(1),
(2), (4) Date: Aug. 30, 2005

(87) PCT Pub. No.: WO03/106484

PCT Pub. Date: Dec. 24, 2003

(65) Prior Publication Data

US 2006/0099588 A1    May 11, 2006

(30) Foreign Application Priority Data

Jun. 17, 2002  (DK) ............................... 2002 00922

(51) Int. Cl.
*C12N 1/15* (2006.01)
*C12N 15/00* (2006.01)
*C07K 14/00* (2006.01)
*C12N 1/00* (2006.01)

(52) U.S. Cl. ................. 435/254.11; 530/350; 435/69.1; 435/69.7

(58) Field of Classification Search .................. None
See application file for complete search history.

(56) References Cited

U.S. PATENT DOCUMENTS 5,800,849 A     9/1998  Budtz et al.
6,127,142 A  *  10/2000 Harboe et al. .............. 435/68.1

FOREIGN PATENT DOCUMENTS

| EP | 0 123 928 | 11/1984 |
| WO | WO 01/14571 | 3/2001 |
| WO | WO 02/02597 | 1/2002 |
| WO | WO 02/063015 | 8/2002 |
| WO | WO 03/054186 | 7/2003 |

OTHER PUBLICATIONS

Korman et al. Cloning, characterization, and expression of two alpha-amylase genes from *Aspergillus niger* var. *awamori*. Curr. Genet. 17: 203-212, 1990.*

Kasturi et al. Regulation of N-linked core glycosylation: use of a site-directed mutagenesis approach to identify Asn-Xaa-Ser/Thr sequons that are poor oligosaccharide acceptors. Biochem. J. 323: 415-419, 1997.*

Ward et al, "Improved production of chymosin in aspergillus by expression as a glucoamylase-chymosin fusion", Bio/Technology 8:435-440 (1990).

Sagt et al, "Introduction of an N-glycosylation site increases secretion of heterologous proteins in yeasts", Applied and Environmental Microbiology 66(11):4940-4944 (2000).

Cardoza et al, "Expression of synthetic copy of the bovine chymosin gene in *Aspergillus awamori* from constitutive and pH-regulated promoters and secretion using two different pre-pro sequences", Biotechnology and Bioengineering 83(3):249-259 (2003).

Wallis et al, "Glucoamylase overexpression and secretion in *Aspergillus niger*: analysis of glycosylation", Biochmica et Biophysica Acta. 472(3):576-586 (1999).

Dunn-Coleman et al, "Commercial Levels of Chymosin Production by *Aspergillus*", Bio/Technology 9:976 (1991).

Harboe, Marianne K., "*Rhizomucor miehei* Aspartic Proteinases Having Improved Properties", Aspartic Proteinases, edited by James, Plenum Press, New York, pp. 293-296 (1998).

Gilliland et al, "The Three-Dimensional Structure of Recombinant Bovine Chymosin at 2.3 Å Resolution", Proteins: Structure, Function, and Genetics 8:82-101 (1990).

Peberdy, John F., "Protein secretion in filamentous fungi—trying to understand a highly productive black box", Tibtech 12:50-57 (1994).

Jenkins and Curling, "Glycosylation of recombinant proteins: Problems and prospects", Enzyme Microb. Technol. 16:354-364 (1994).

Berka et al, "The development of *Aspergillus niger* var. *awamori* as a host for the expression and secretion of heterologous gene products", Biochemical Society Translations, vol. 19(3):681-685 (1991)—XP002256358.

* cited by examiner

*Primary Examiner*—Michele K Joike
(74) *Attorney, Agent, or Firm*—Nixon & Vanderhye P.C.

(57) ABSTRACT

A polypeptide comprising an aspartic protease such as chymosin which is modified so as to comprise at least one —N—X-T-glycosylation site and a method for producing such a polypeptide.

22 Claims, 3 Drawing Sheets

Figure 1:
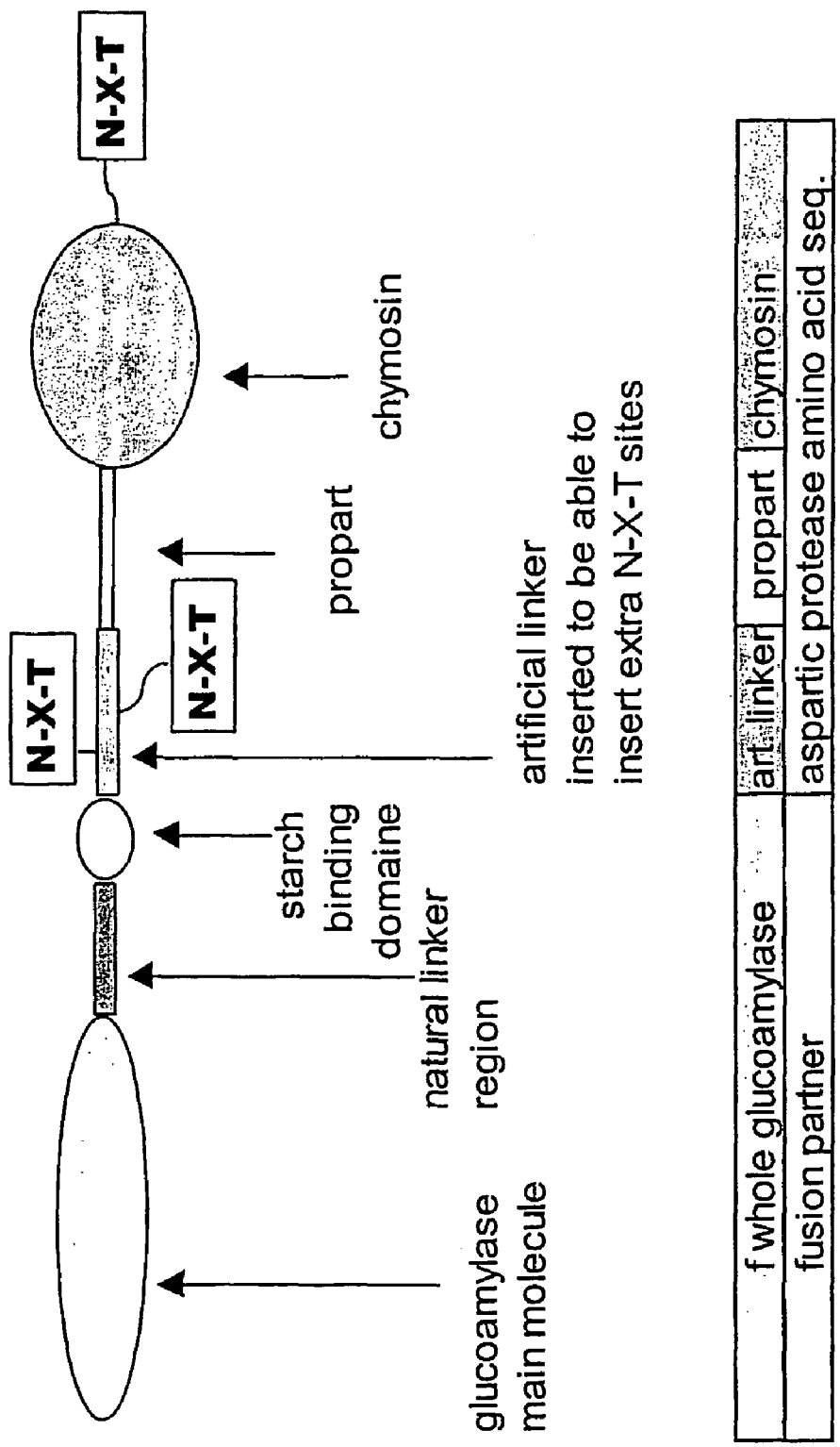

The mutation as introduced in fragment modB-XS is indicated in bold (g-c)

*SalI*
cggtcgaccgctacggtgactgacacctggcgtgccgagatcactcgcatcccctctacaaggg:aagtctctgcgtaaggctctca
*XhoI*
aggagcacggtctgctcgaggatttcctgcagaagcagcagtacggcatcagctctaagtacagc;;gtttcggcgaggtggccagcg
tgcctctcactaactacctggacagccagtacttcggtaagatctaccttggcactcccctcaggagttcaccgttctgttcgatactggt
tccagcgacttctgggttccctccatctactgtaagagcaacgcttgcaagaaccaccagcgcttcg;tcctcgcaagtccagcaccttc
*SphI*
cagaaccttggcaagcccctttccatccactacggtactggcagcatgcagggtatccttggctacgacaccgttaccgtgtccaacat
cgtcgatattcagcagaccgtgggtctgagcacccaggagcctggcgatgtcttcacttacgccga;ittcgatggtatcctcggcatgg
*Bsr*
cttacccctccctggcctctgagtactctatccctgtgttcgacaacatgatgaaccgccacctcgtcgctcaggatctgttcagcgtgta
*GI*
catggaccgtaacggtcaggagtccatgcttactctgggcgccatcgatccctcttactacaccggttccctccactgggttcctgtgac
cgtccagcagtactggcagttcaccgtggacagcgtcactatctccggcgtggttgtggcttgcgagggtggctgtcaggccatccttg
atactggtaccagcaagctcgtcggcccctccagcgacatcctgaacatccagcaggctatcggtg;cacccagaaccagtacggcg
agttcgatatcgactgcgataaccttcttacatgcctactgtggttttcgagatcaacggtaagatgta::cccttactccttctgcttacact
tcccaggatcagggcttctgtacctctggtttccagtctgagaaccacagccagaagtggatccttggcgatgtcttcatccgcgagtact
*XbaI*
actccgtcttcgaccgtgccaacaacctggtgggtctcgctaaggccatctgatcctctagagt

Fig. 2

SEQ ID NO:3 cggtcgaccgctacggtgactgacacctggcgtgccgagatcactcgcatcccctctacaagggcaagtctctgcgtaaggctctca
aggagcacggtctgctcgaggatttcctgcagaagcagcagtacggcatcagctctaagtacagcggtttcggcgaggtggccagcg
tgcctctcactaactacctggacagccagtacttcggtaagatctaccttggcactcccctcaggagttcaccgttctgttcgatactggt
tccagcgacttctgggttccctccatctactgtaagagcaacgcttgcaagaaccaccagcgcttcgatcctcgcaagtccagcaccttc
cagaaccttggcaagccccttccatccactacggtactggcagcatgcag

SEQ ID NO:4 gcagcatgcagggtatccttggctacgacaccgttaccgtgtccaacatcgtcgatattcagcagaccgtgggtctgagcacccagga
gcctggcgatgtcttcacttacgccgagttcgatggtatcctcggcatggcttaccctccctggcctctgagtactctatccctgtgttcg
acaacatgatgaaccgccacctcgtcgctcaggatctgttcagcgtgtacatg

SEQ ID NO:5 gcgtgtacatggaccgtaacggtcaggagtccatgcttactctgggcgccatcgatccctcttactacaccggttccctccactgggttc
ctgtgaccgtccagcagtactggcagttcaccgtggacagcgtcactatctccggcgtggttgtggcttgcgagggtggctgtcaggcc
atccttgatactggtaccagc

SEQ ID NO:6 ctggtaccagcaagctcgtcggcccctccagcgacatcctgaacatccagcaggctatcggtgccacccagaaccagtacggcgag
ttcgatatcgactgcgataaccttcttacatgcctactgtggttttcgagatcaacggtaagatgtaccccccttactccttctgcttacacttc
ccaggatcagggcttctgtacctctggtttccagtctgagaaccacagccagaagtggatccttggcgatgtcttcatccgcgagtacta
ctccgtcttcgaccgtgccaacaacctggtgggtctcgctaaggccatctgatcctctagagt

SEQ ID NO:7 ctggtaccagcaagctcgtcggcccctccagcgacatcctgaacatccagcaggctatcggtgccacccagaaccagtacggcgag
ttcgatatcgactgcgataaccttcttacatgcctactgtggttttcgagatcaacggtaagatgtaccccccttactccttctgcttacacttc
ccaggatcagggcttctgtacctctggtttccagtctgagaaccacacccagaagtggatccttggcgatgtcttcatccgcgagtacta
ctccgtcttcgaccgtgccaacaacctggtgggtctcgctaaggccatctgatcctctagagt

SEQ ID NO:8 ggccaggcgcgccttccatggaagaatgcggccgctaaaccatcgatggctcgagttggcgcgcca

Fig. 3

METHOD OF PRODUCING AN ASPARTIC PROTEASE IN A RECOMBINANT HOST ORGANISM

This application is the U.S. national phase of international application PCT/DK03/00398 filed on 16 Jun. 2003, which designated the U.S. and claims priority to DK Application No. PA 2002 00922 filed 17 Jun. 2002. The entire contents of these applications are incorporated herein by reference.

FIELD OF INVENTION

The present invention relates generally to the field of polypeptides and in particular to aspartic proteases such as e.g. chymosin. Specifically, the invention pertains to novel recombinant means of improving the production and/or secretion of polypeptides, in particular aspartic protease, which is modified in at least one glycosylation site.

PRIOR ART AND TECHNICAL BACKGROUND

A wide variety of prokaryotic and eukaryotic hosts exist and is available for the expression of heterologous genes. The features of importance for selecting an appropriate host depend on the characteristic of the protein to be produced and the applications hereof. It appears that filamentous fungi possess unique features, which make them attractive as host organisms for the production of heterologous gene products. It is furthermore known by a person of skill that certain fungal species are capable of secreting large quantities of proteins in submerged cultures. In 1991, selected strains of Aspergillus niger can produce greater than 20 g of glucoamylase per liter in industrial fermentations. During the last decade, the use of filamentous fungi for the expression and secretion of heterologous proteins has been extensively explored. For example, Berka et al. (1991) disclosed the use of strains of Aspergillus niger var. awamori as hosts for the expression and secretion of bovine chymosin and Rhizomucor miehei aspartyl protease (RmAP), two milk-clotting enzymes used commercially in cheese manufacturing to obtain coagulation (alias clotting) of the milk.

Enzymatic coagulation of milk by milk-clotting enzymes, such as chymosin and pepsin, is obviously one of the most important processes in the manufacture of cheeses. Enzymatic milk coagulation is a two-phase process: a first phase where a proteolytic enzyme, preferably an aspartic protease such as e.g. chymosin or pepsin, attacks κ-casein, resulting in a metastable state of the casein micelle structure and a second phase, where the milk subsequently coagulates and forms a coagulum.

Chymosin (EC 3.4.23.4) and pepsin (EC 3.4.23.1), the milk clotting enzymes of the mammalian stomach, are aspartic proteases that are produced naturally in the gastric mucosal cells of several mammalian species including ruminant species, porcine species, primate species and ungulate species. When produced in the gastric mucosal cells, chymosin occurs as enzymatically inactive pre-prochymosin. When chymosin is excreted, an N-terminal peptide fragment, the pre-fragment (signal peptide) is cleaved off to give pro-chymosin including a pro-fragment. Prochymosin is a substantially inactive form of the enzyme, which however, becomes activated under acidic conditions to the active chymosin by autocatalytic removal of the pro-fragment. The active form is termed the mature form. This activation occurs in vivo in the gastric lumen under appropriate pH conditions or in vitro under acidic conditions.

An insufficient availability of calf stomachs often occurs and a consequence of this is that the price of calf chymosin becomes subject to undesired fluctuations. For these reasons expression of bovine chymosin in microorganisms is very attractive as production method, as it will tend to hamper price level fluctuations and to date bovine chymosin cDNA sequences have been successfully expressed in bacteria, yeast and filamentous fungi.

However, major barriers for achieving higher yields of aspartic proteases such as e.g. chymosin from filamentous fungi unfortunately exist. Examples hereof include proteolytic degradation of the protein by endogenous host aspartyl proteases and inefficient secretion of the heterologous protein product from the fungi.

In order to avoid some of the above barriers, the general practice for production of non-homologous proteins in fungi is to make a fusion of the protein of interest to a highly secreted fungal carrier molecule such as e.g. glucoamylases, or amylases or cellulases. A specific cleavage site is usually introduced between the carrier molecule and the non-fungal protein. One example of such a production system is the production of chymosin by Aspergillus niger var. awamori, in which the prochymosin gene is fused to the fungal carrier glucoamylase (Ward et al., 1990).

The chymosin molecule is well characterised in the prior art. It appears that Chymosin consists of one single chain of 223 amino acids having three disulphide bridges and a molecular weight of approx. 35.000. The amino acid sequence is known. Chymosin exists in at least two iso-forms, viz. A and B. The A-form possesses the amino acid Asp in position 244, whilst the B-form has instead a Gly in the same position.

Chymosin is furthermore featured by having two N—X—S glycosylation sites which however are poorly glycosylated. The degree of glycosylation is shown to be less than 1%, when chymosin is produced in a bovine animal versus a degree of about 10% when produced by fermentation of a genetically modified Aspergillus niger var. awamori All aspartic proteases consist of two similar domains packed in such a manner that a deep active site cleft is formed. It appears that the amino acid Asp (nos 34 and 216, when reffering to chymosin) are the main amino acids participating in the catalysis, but also Tyr75, situated on a loop, the so-called flap, seems to influence the activity of the enzymes (Gilliland et al., 1990)

In the prior art there are conflicting opinions on whether or not the glycosylation of heterologous proteins improves the secretion of the protein from the host. Although most prior art may seem to link an improved secretion with a glycosylation of the protein (Berka et al., 1991), some authors state that the protein glycosylation may not be a prerequisite for obtaining an enhanced glycoprotein production and/or secretion from the host (Wallis et al. 1999).

According to current prior art the basic glycosylation involves the attachment of oligosaccharides to Asn (Jenkins and Curling, 1994), Ser and Thr residues in the consensus sequence Asn-X-Ser/Thr on the surface of the molecules. The oligosaccharides attached to Asn residues are referred to as N-linked, whereas those attached to Ser and Thr are designated as O-linked oligosacchaides. The N-linked glycans, which in general is to be understood as monosaccharides linked together by glycosidic bonds, have in the present context a core region of two N-acetylglucosamine residues, which provide the linkage to the protein, joined with eight mannose residues. From a review of protein secretion (Peberdy, 1994) it appears that the O-linked glycosylation of a protein is essential for the secretion, whilst the N-linked oligosaccharides appears to be of importance when providing the protein with stability and resistance to environmental influence.

Thr at position 3 in the consensus sequence Asn-X-Ser/Thr seems to lead to an increased chance of glycosylation compared to Ser at this position (Jenkins and Curling, 1994). Furthermore, several other factors may be important for the glycosylation, i.e. the position (susceptibility) of the Asn in the three-dimensional structure and different production organisms glycosylate differently (Harboe, 1998).

It appears from the prior art that it has been suggested to improve secretion of heterologous proteins produced in filamentous fungi by means of an introduction of glycosylation sites. By way of example Berka et al. (1991) demonstrate in a study that the chymosin coding region was modified by introduction of a consensus N-linked N—X—S glycosylation site ($Ser^{74} \rightarrow Asn^{74}$, $His^{76} \rightarrow Ser^{76}$) in a chymosin molecule that had a very low glycosylation of the two potential glycosylation sites on chymosin and no fusion partner. It was found that the production yields of extracellular chymosin were increased at least three-fold compared with the parental native chymosin having only two poorly glycosylated sites. However, it furthermore appeared that the specific activity of the so-called glycochymosin was reduced to about 20% relative to that of the native chymosin. It is evident from the wording that the experimental work was conducted in a laboratory scale and that the outcome was very low chymosin yields. One conclusion from this work is that the yield was improved from low yield to still low yield of secreted chymosin.

As the specific activity additionally dropped significantly, it must be concluded that the non-conservative substitutions conducted by Berka, are to be accorded other effects on the enzyme activity and properties.

To date, improved glycosylation has not been publicly used and described to obtain commercial levels of protein production, assumingly because it has been observed and established as an undisputed fact that increased enzyme production due to glycosylation was accompanied by severely decreased specific enzyme activity, making this a non-attractive production method.

Hitherto it appears from the prior art that no method has been disclosed whereby the production capacity of the enzyme activity is increased in this context by alteration of the glycosylation of aspartic protease such as e.g. chymosin without influencing the enzyme properties.

SUMMARY OF THE INVENTION

The problem to be solved by the present invention is to provide a method to get increased production yields of a recombinantly produced aspartic protease, such as e.g. chymosin, without substantially influencing the aspartic protease enzyme properties as such.

The solution is based on that the present inventors have identified that it has been found that the recombinant production capacity of an aspartic protease, such as e.g. chymosin, can be increased by an alteration of a specific glycosylation site. More specifically, by incorporating a new N—X-T glycosylation site into a polypeptide comprising an aspartic protease amino acid sequence. In working example 1 herein a new N—X-T glycosylation site is incorporated into the active mature part of an aspartic protease and in working example 3 a new N—X-T glycosylation site is incorporated into a linker sequence situated upstream of a pro-fragment of an aspartic protease. FIG. 1, illustrates schematically these working examples. In both cases the result was increased yields of the recombinantly produced aspartic protease without significantly reducing the activity of the enzyme as compared to its native counterpart.

Without being limited to theory, it is believed that the fact that the N—X-T glycosylation site has been incorporated at very different places, both within and outside the mature part of the aspartic protease supports that the present inventors have identified a new general concept. In other words the N—X-T glycosylation site may be incorporated at numerous different places and still give the desired increased yields.

The polypeptide comprising an aspartic protease amino acid sequence is encoded by a DNA sequence and the DNA sequence has been modified to have a DNA sequence encoding a N—X-T glycosylation site.

Accordingly, a first aspect of the invention relates to a process for obtaining an isolated polynucleotide sequence comprising a DNA sequence encoding a polypeptide comprising an aspartic protease amino acid sequence, wherein the process comprises the steps of modifying the polynucleotide sequence to encode an extra polypeptide N—X-T glycosylation site in the aspartic protease amino acid sequence and isolating the modified polynucleotide sequence encoding a modified polypeptide.

The term "modifying the DNA sequence" denotes simply the actual work in order to change the specific sequence of the DNA to encode an extra polypeptide N—X-T glycosylation site. There are numerous different specific protocols for doing this and the skilled person is aware of choosing the most adequate one for his specific needs.

The term "extra" denotes that the N—X-T glycosylation site is new (extra) as compared to before the DNA sequence was modified. "The term "an extra" should be interpreted as covering one or more extra glycosylation site(s). In other words at least one extra glycosylation site. The term extra may also refer to a modified glycosylation site.

The term "an aspartic protease amino add sequence" denotes a sequence that is capable of being an active aspartic protease. It may be a mature active aspartic protease amino acid sequence. Alternatively, an aspartic protease amino acid sequence may be the mature sequence plus a pro-sequence. Such a sequence is not completely enzymatic active but capable of being converted into an active aspartic protease by autocatalytic removal of the pro-fragment (see above). Similarly, an aspartic protease amino acid sequence may be a sequence comprising a pre-sequence, pro-sequence, and the mature sequence. Further, within the term aspartic protease amino acid sequence is a sequence that may further comprise an artificial linker sequence comprising a N—X-T glycosylation site. The artificial linker sequence is a sequence that does not exhibit any enzymatic activity in itself. The artificial linker sequence should be situated in connection with a sequence that corresponds to an active element of an aspartic protease sequence. An active element may be a pre-sequence, a pro-sequence or a mature sequence. An example of an artificial linker sequence within "an aspartic protease amino acid sequence" as defined herein is illustrated in FIG. 1. Here the artificial linker sequence is situated in connection with a pro-sequence. An N—X-T glycosylation site of the artificial linker should preferably be situated within 100 amino acids (more preferably 60 amino acids, even more preferably 35 amino acids, most preferably 15 amino acids) of the most closely situated active element of an aspartic protease sequence. The artificial linker sequence may be situated N-terminal of the mature sequence or C-terminal of the mature sequence.

The term "an isolated polynucleotide sequence" refers to a DNA sequence cloned in accordance with standard cloning procedures used in genetic engineering to relocate a segment of DNA from its natural location to a different site where it will be reproduced. The cloning process involves excision and isolation of the desired DNA segment, insertion of the piece of DNA into the vector molecule and incorporation of the recombinant vector into a cell where multiple copies or clones of the DNA segment will be replicated. The "isolated polynucleotide sequence" of the invention may alternatively be termed "cloned polynucleotide sequence".

The isolated polynucleotide sequence of the first aspect is a novel DNA sequence.

Accordingly, a second aspect of the invention relates to an isolated polynucleotide sequence comprising a DNA sequence encoding a polypeptide comprising an aspartic protease amino acid sequence, obtainable by a process for obtaining an isolated polynucleotide sequence as described herein.

An advantage of the incorporation of the extra polypeptide N—X-T glycosylation site is that increased yield of recombinantly produced aspartic protease may be obtained.

Consequently, in a third aspect the invention relates to a method of producing a polypeptide exhibiting aspartic protease activity comprising the steps of cultivating a host organism comprising an isolated polynucleotide sequence of the second aspect of the invention and isolating the produced polypeptide exhibiting aspartic protease activity.

The term "exhibiting aspartic protease activity" denotes an activity that substantially corresponds to the activity of a mature active aspartic protease. An aspartic protease amino acid sequence wherein the pro-sequence is not cleaved off is not a polypeptide exhibiting aspartic protease activity.

As said above, an aspartic protease, such as a chymosin comprises two N—X—S glycosylation sites and no N—X-T glycosylation sites.

Accordingly, in a fourth aspect the present invention relates to an isolated polypeptide exhibiting aspartic protease activity comprising a N—X-T glycosylation site.

As defined herein the term, "an isolated polypeptide" as used to describe the aspartic protease of the invention, is an aspartic protease or aspartic protease part that is substantially free from other non-aspartic protease polypeptides. Preferably, it is at least 5% pure, preferably at least 20% pure, more preferably 50% pure, even more preferably 75% pure, most preferably 90% pure, and even most preferably 95% pure, as determined by SDS-PAGE. Further, "an isolated polypeptide" as used about the aspartic protease of the invention, is preferably an aspartic protease or aspartic protease part that is substantially free from homologous impurities. A heterologous recombinant production of an enzyme makes it is possible to make an isolated enzyme preparation, characterized in being free from homologous impurities. As used herein the term "homologous impurities" means any impurity (e.g. another polypeptide than the enzyme of the invention), which originates from the homologous cell from which the enzyme of the invention is originally obtained. If the aspartic protease is e.g. a bovine chymosin the homologous cell may e.g. be a bovine cell. Heterologous recombinant production using e.g. filamentous fungi as host organism would provide an isolated bovine chymosin polypeptide substantially free from homologous impurities.

Finally, the present invention relates to an isolated polypeptide exhibiting aspartic protease activity wherein the polypeptide has been modified to comprise an extra N—X-T glycosylation site.

DETALED DISCLOSURE OF THE INVENTION

The present invention provides in one aspect a method to achieve an enhanced amount of secreted heterologous proteins, in particular aspartic proteases, from eukaryotic hosts. This improved yield of secreted protein has been surprisingly accomplished by modifying a polypeptide coding for an aspartic protease said polypeptide being modified so as to comprise at least one additional —N—X-T-glycosylation site.

In one preferred embodiment, the polypeptide comprises an aspartic protease, which is a mammalian chymosin. It is to be appreciated that the invention encompasses both natural mammalian chymosin or nature-identical chymosin and non-natural mammalian chymosin. In the present context, the expression "non-natural mammalian chymosin" relates to a chymosin molecule, which not normally is found in nature. Such a chymosin molecule may include a chimeric chymosin molecule, which is encoded and formed, by e.g. recombinant DNA techniques, from nucleic acids derived from organisms, which do not normally exchange genetic information, e.g. a ruminant species and a *Camelidae* species. Additionally, a non-natural mammalian chymosin may also include a chymosin molecule encoded by a cluster or a shuffling of DNA segments of different origin resulting in complex rearrangements of the DNA. Accordingly, in a further embodiment of the present invention the polypeptide may comprise a mammalian chymosin molecule that is composed of at least two different chymosin molecules derived from mammalian species.

In preferred embodiments, the polypeptide comprises a mammalian chymosin molecule which is modified and derived from a mammalian species selected from the group consisting of a ruminant species, a *Camelidae* species including *Camelus dromedarius*, a porcine species, an *Equidae* species and a primate species. A ruminant species source animal may be selected from bovine species, camel species, deer species, buffalo species, antelope species, giraffe species, ovine species and caprine species. A particularly interesting source animal is *Camelus dromedarius*.

The person skilled in the art will readily appreciate that any polypeptide comprising preprochymosin, prochymosin or chymosin will be useful in the present invention. When produced in the stomach tissues cells chymosin occurs as an enzymatically inactive pre-enzyme, which is designated preprochymosin. When chymosin is excreted, an N-terminal fragment is cleaved off to give prochymosin including a pro-fragment. Prochymosin is essentially inactive form of the enzyme, which, however, under acidic conditions becomes activated to the active chymosin molecule by removal of the pro-fragment. Thus, in preferred embodiments, the polypeptide comprises a chymosin, which is selected from the group consisting of pre-prochymosin, prochymosin, and chymosin.

Another suitable aspartic protease is Pepsin (EC 3.4.23.1). At the filing date of the present invention the SWISS-PROT database comprised following entries to sequences of suitable pepsins:

(Primary accession number, Entry name)
P03954, PEP1_MACFU; P28712, PEP1_RABIT; P27677, PEP2_MACFU;
P27821, PEP2_RABIT; P27822, PEP3_RABIT; P27678, PEP4_MACFU;
P28713, PEP4_RABIT; P00792, PEPA_BOVIN; Q9N2D4, PEPA_CALJA;
P00793, PEPA_CHICK; P00790, PEPA_HUMAN; P11489, PEPA_MACMU;
P00791, PEPA_PIG; P81497, PEPA_SUNMU; P13636, PEPA_URSTH;
P27823, PEPF_RABIT.

As for chymosin, a preferred pepsin is a pepsin derived from the group consisting of ruminant species. See above for preferred specific species that corresponds to the preferred ones for chymosin.

A further suitable aspartic protease is a protease selected from the groub consisting of Pepsin A (EC 3.4.23.1), Cryphonectriapepsin (EC 3.4.23.22), and Rhizomucorpepsin (EC 3.4.23.23). As for chymosin, a preferred protease of this selected group is a protease derived from the group consisting of ruminant species.

In accordance with the present invention the glycosylated aspartic protease has at least one —N—X-T-glycosylation site. For the purposes of this application, the expression "—N—X-T-glycosylation site" relates to a glycosylation site in the aspartic protease, where "N" designates the amino acid asparagine (Asn), "X" any kind of amino acid and "T" designates the amino acid threonine (Thr). In a preferred embodiment, the polypeptide is modified so as to comprise at least one N-glycosylation site, i.e. the oligosaccharides is attached to an Asn residue.

In the present context, the term "modified so as to comprise at least one —N—X-T-glycosylation site" is to be construed to comprise, relative to the native or parent polypeptide from which the polypeptide according to the invention is derived, any modification of the codons in the nuceic acid sequence coding for an aspartic protease which results in at least one additional —N—X-T-glycosylation site. It is thus prescribed in the present invention to insert or modify such recognition or glycosylation site in the sequence of the native or parent aspartic protease. Any such modification or any change of the codon usage may be based on recombinant DNA-technology using e.g. two approaches. According to a first approach the alteration of the codon usage is restricted to certain stretches of the coding sequence (primarily based on oligonucleotide design and PCR) and another approach wherein the entire coding sequence becomes optimised (primarily based on an assembly of designed oligonucleotides representing the entire coding sequence). The skilled artisan will readily appreciate that further approaches for obtaining such a modification are known in the art and can be used as comprised by the present invention.

During the experimentation leading to the highly unexpected finding that an aspartic protease, such as e.g. chymosin, which is modified so as to comprise at least one additional N—X-T glycosylation site, i.e. a glycosylated aspartic protease variant, secreted in significantly higher yields of enzyme activity such as e.g. milk clotting activity relative to an unmodified or parent aspartic protease having the same number of glycosylation sites on the chymosin part and/or one additional glycosylation site on the linker region when expressed in the same host cell and under essentially identical conditions. Thus, in one preferred embodiment of the present invention, the polypeptide is one wherein the at least one —N—X-T-glycosylation site is provided by modifying one or more codons in a nucleic acid sequence coding for a naturally produced chymosin molecule.

In useful embodiments, the nucleic acid sequence coding for a naturally produced chymosin molecule is selected from the group consisting of a wild-type nucleic acid sequence and a nucleic acid sequence which is derived from a wild-type nucleic acid sequence by silently modifying at least one codon.

When producing aspartic proteases by recombinant means it is desirable that the produced heterologous proteins exhibits substantially the same functionality which preferably may be improved compared to the native or parent protein from which the recombinant aspartic protease is derivable. It is thus an important feature of the present invention that the polypeptide comprising the glycosylated aspartic protease has substantially the same functionality as the parent aspartic protease. In the present context, the expression "substantially the same functionality" indicates that although the resulting polypeptide comprising the aspartic protease differs from the aspartic protease from which it is derived by one or more amino acids, the glycosylated aspartic protease variant is a functional analogue of the parent aspartic protease from which it is derived and thus possesses substantially the same enzymatic activity either before or after a deglycosylation treatment as discussed below.

Thus, during their experiments, the inventors of the present invention uncovered sites in the aspartic protease molecule suitable for introducing one or more glycosylation sites.

When herein referred to "the chymosin numbering described in Gilliland (1990)" it corresponds to the numbering as shown in SEQ ID NO 1.

The Aspartic acid proteinase generally share a bi-lobal fold composed of the N-terminal and the C-terminal domain. There secondary structure primarily consisting of beta sheets and a few alpha helices (Gilliland (1990)). The active site is embedded between the two domains, in the middle of an app. 40 Å wide cleft, covered by a highly flexible flap. Chymosin exist in two alternatively structural forms, the self-inhibited form where the S1 and S3 binding pocket is occluded by Tyrosine 77 situated in the flap-region (Gustchina E. et al.) and the active form where with the binding pocket is free to bind the substrate. The regions surrounding the active site enclose other flexible loops i.e. for chymosin amino acid residues 11-14, 159-163, 241-249, 278-282 and 288-294 (Gilliland (1990) numbering) that also is involved in the conformation changes during binding of the substrate. Insertion of NXT sites in these regions can alter the dynamic thereby affect activity and stability. These regions are preferref region to insert a NXT site. One example will be reduction of the access to the active site and thereby making the molecule more dependent of the allosteric activation by the k-casein His-Pro region.

Positioning of NXT glycosylation sites at the aspartic acid protease surface will be of interests in many aspects. The surface charge distribution of chymosin, that provide a positive patch within amino acid residues 48-62 and a negatively charge loop in the amino acid residues 241-249 which are proposed to contribute to the electrostatic stabilization of the enzyme substrate complex. Glycosylation in these regions is likely to put further restrains to the enzymes activity. In general glycosylation situated in charged areas would affect close intermolecular electrostatic interactions.

Chymosin has an extremely hydrophobic nature. Production of hydrophobic proteins is more difficult in general. One way to improve chymosin production levels is to reduce it's hydrophobicity, e.g. by replacing some hydrophobic amino acids by a glycosylation site. Since glycosylation groups are bulky side chains it is important to place such a group outside regions important for the enzymatic activity or for binding of the substrate, casein.

Preferably the three hydrophobic amino acids of position 203-205 (VVV) is replaced by an NXT site, preferably a NTT site.

Shielding of hydrophobic patches i.e. chymosin surface exposed disulfide bond of $Cys_{250}$-$Cys_{283}$ by insertion glycosylation will provide altered the molecular behavior e.g. with respect to stability and solubility. These are also preferred sites to insert a NXT glycosylation site.

As shown in the Examples below, the inventors found the yield of the heterologous produced aspartic protease to be especially effective when a glycosylation site was modified at a specific position of the aspartic protease such as e.g. a chymosin molecule. In a preferred embodiment, the polypeptide is one wherein the at least one —N—X-T-glycosylation site is introduced at position 291-293 of the native or parent chymosin molecule according to the chymosin numbering described in Gilliland (1990). In a further embodiment, the polypeptide is one wherein the nucleic acid sequence coding for the naturally produced chymosin is modified by substituting $S_{293}$ with T creating a NXT glycosylation site.

According to the present invention the parent polypeptide comprising an aspartic protease may be any polypeptide which may prove to be useful in a widespread applications, such as e.g. within the food or medical industry.

The expression "parent polypeptide comprising an aspartic protease" in the present context shall include any polypeptide coding for an aspartic protease, such as wild-type aspartic protease or a variant thereof, which are substantially functional and/or structural, identical to the aspartic protease encoded by the polypeptide.

It is generally known in the art that expressing the gene product in the form of a fusion protein can enhance expression and secretion of a heterologous gene product. In this context, the term "fusion protein" denotes a chimeric protein comprising as one part an aspartic protease amino acid sequence such as e.g. pre-prochymosin, prochymosin, artificial linker-prochymosin, or chymosin or at least a milk coagulation active part hereof, and as a second part a fusion partner. The term "aspartic protease amino acid sequence" is described above and the term fusion partner is in this context to be understood as any polypeptide to which the aspartic protease amino acid sequence is being fused. Accordingly, in one embodiment of the invention, the gene product comprises a fusion protein. Useful fusion partners may be a secreted fungal carrier such as one selected from the group consisting of glucoamylase, alpha-amylase, cellobiohydrolase and a part or fragment thereof. In one specific embodiment, the polypeptide comprises a fusion protein, which consists of glucoamylase and pro-chymosin. FIG. 1 illustrates schematically a fusion protein comprising glucoamylase as fusion partner. The fusion partner may be situated N-terminal of the mature sequence or C-terminal of the mature sequence.

The term "aspartic protease amino acid sequence" is preferably not including the sequence of the fusion partner.

The inventors of the present invention found increased production yields when producing a nature-like aspartic protease, under certain circumstances viz. by introduction of an artificial linker-sequence between the nucleotide sequence encoding the carrier molecule e.g. glucoamylase, and by using the nucleotide sequence coding for the aspartic protease of interest. An example of such a linker is shown in the below Examples, where said linker contains an additional —N—X-T-glycosylation site. In this way, it was found that the fusion aspartic protease is more heavily glycosylated and thus will be produced and secreted at higher levels by the host relative to a aspartic protease produced without a linker between nucleotide sequence coding for the fusion partner and the aspartic protease. Furthermore, the fusion aspartic protease is fully identical to the natural aspartic protease. The aspartic protease of interest is released specifically from the fusion partner by a determined cleavage, which takes place during the secretion or while in the culture medium. This specific cleavage must occur at the C-terminal of the linker sequence to obtain a nature identical aspartic protease. Accordingly, in a useful embodiment, the polypeptide comprises a fusion aspartic protease where glucoamylase and aspartic protease are separated by an artificial linker, said linker comprises preferable a glycosylation site such as a —N—X-T-glycosylation site.

As mentioned above, the present invention is particularly suitable for the provision of an improvement of the glycosylation of heterologously produced proteins or of their fusion partners, such as e.g. aspartic proteases in order to increase the production of said aspartic protease. In preferred embodiments, the polypeptide comprising an aspartic protease according to the invention is, when it is expressed in a filamentous fungus, at least 10% glycosylated, such as at least 20%, e.g. at least 30% including at least 40% such as at least 50%, e.g. at least 60% including at least 70%, such as at least 80%, e.g. at least 90% or even 100% glycosylated relative to polypeptide comprising an aspartic protease which is not modified so as to comprise at least one —N—X-T-glycosylation site. In further embodiments, the polypeptide comprising an aspartic protease according to the invention is, when it is expressed in *Aspergillus niger* var. *awamori*, at least 10% glycosylated, such as at least 20%, e.g. at least 30% including at least 40% such as at least 50%, e.g. at least 60% including at least 70%, such as at least 80%, e.g. at least 90% or even 100% glycosylated relative to polypeptide comprising an aspartic protease which is not modified so as to comprise at least one —N—X-T-glycosylation site.

It is generally known in the art that the glycosylation of polypeptides, when these are heterologous expressed by an eukaryotic host, may have a reduced enzymatic activity compared to the pertinent natural polypeptide. It has been found (Berka et al. 1991) that the enzymatic activity of aspartic proteases of microbial origin that are glycosylated upon expression may be enhanced by subjecting the proteases to a deglycosylating treatment that at least partially removes the sugar moieties attached to the proteases. Such a deglycosylation treatment may e.g. comprise treating the glycosylated protease with an enzyme having a deglycosylating activity. Examples of enzymes having a deglycosylation activity comprise PNGase and endo-β-N-acetylglucosaminidase (EC 3.2.1.96) (Endo-H). Alternatively, the deglycosylation may be accomplished by subjecting the glycosylated proteases to a chemical treatment, such as e.g. treatment with periodate.

In a specific embodiment, the polypeptide comprising an aspartic protease has a milk-clotting activity of which is, relative to the glycosylated polypeptide, increased by at least 20%, e.g. at least 30% including at least 40% such as at least 50%, e.g. at least 60% including at least 70%, such as at least 80% when subjecting it to a deglycosylation treatment.

It is furthermore contemplated by the present invention that deglycosylation of an expressed aspartic protease may be obtained in a more direct manner by providing a host cell that in addition to the aspartic protease also expresses a deglycosylating enzyme such as e.g. Endo-H, which Implies that the initially glycosylated aspartic protease is deglycosylated either intracellularly or following secretion.

As mentioned above, one major objective of the present invention is to provide a method for improving the production and/or secretion of aspartic proteases in host organisms including filamentous fungi. Accordingly, in a further aspect there is provided a method of producing an isolated polypeptide exhibiting aspartic protease activity comprising the steps of cultivating a host organism comprising an isolated polynucleotide sequence of the second aspect of the invention and isolating the produced polypeptide exhibiting aspartic protease activity.

In an initial step of this method, a nucleic acid sequence, i.e. a polynucleotide that codes for an aspartic protease including pre-prochymosin, prochymosin or chymosin modified as defined above is provided. The skilled artisan will appreciate that several approaches for providing a parent sequence for such a modified sequence can be used including one based on the isolation of mRNA from mucosal cells of the selected source animal species and using this RNA as template in a nucleotide amplification procedure such as a PCR reaction using suitable sense and anti-sense primers which e.g. may be constructed synthetically based on the known sequences for selected species. The person of skill in the art will appreciate that other methods for obtaining a parent coding sequence which can be modified according to the invention may be used such as hybridisation procedures using as probes fragments of known coding sequences for the aspartic protease that will permit the presence of homologous DNA or RNA to be detected in preparations of cells of the selected source species. Alternatively, it is possible to construct a parent coding sequence based on the isolation of the aspartic protease including pre-prochymosin, prochymosin or chymosin followed by determining the amino acid sequence of the enzyme or fragments hereof which in turn permits the construction of primer oligonucleotides for detection and construction of coding sequences. The basic techniques that are required in the above procedures of obtaining coding sequences are generally within the common knowledge of the skilled artisan (Sambrook et al., 1989).

Having isolated or constructed the parent sequence coding for the aspartic protease including pre-prochymosin, prochymosin or chymosin and subsequently modified said coding sequence so as to comprise at least one —N—X-T-glycosylation site as defined above, an expression vector may be constructed that comprises the coding sequence according to the invention and, operably linked thereto, appropriate expression signals, i.e. sequences to control or regulate the expression, permitting the aspartic protease to be expressed in a selected host cell. A suitable expression vector may comprise one or more expression signals such as promoter sequences, operators, ribosome binding sites, translation initiation sites and/or sequences coding for repressor or activator substances. To permit the secretion of the expressed polypeptide, a signal sequence may be inserted upstream of the coding sequence for the aspartic protease or the expressed polypeptide may be fused to a naturally secreted endogenous polypeptide. In the present context, the term "expression signal" includes any of the above control sequences, repressor or activator substances and signal sequences. For expression under the direction of control sequences, the coding sequence is operably linked to the control sequences in proper manner with respect to expression.

In accordance with the invention, an expression vector carrying the coding sequence or polypeptide coding for the aspartic protease as defined above can be any vector that is capable of expressing the coding sequence in the selected host organism, and the choice of vector type will depend on the host cell into which it is to be introduced. Thus, the vector may be an autonomously replicating vector, i.e. a vector that exists as an extrachromosomal entity, the replication of which is independent of chromosomal replication in the host cells, e.g. a plasmid, a viral vector, a minichromosome or an artificial chromosome. Alternatively, the vector may be a vector which, when introduced into a host cell, is integrated into the host cell genome and replicated with the chromosome, including a transposable element.

In the vector, the polypeptide coding for the aspartic protease is operably combined with a suitable promoter sequence. The promoter may be any DNA sequence, which confers transcriptional activity to the host organism of choice and may be derived from genes encoding proteins, which are either homologous or heterologous to the host organism.

For transcription in a fungal species, examples of useful promoters are those derived from the genes encoding the *Pichia pastoris* alcohol oxidase, *Aspergillus oiyzae* TAKA amylase, *Rhizomucor miehei* aspartic proteinase, *Aspergillus niger* neutral α-amylase, *Aspergillus niger* acid stable α-amylase, *A. niger* glucoamylase, *Rhizomucor miehei* lipase, *Aspergillus oryzae* alkaline protease, *Aspergillus oryzae* triose phosphate isomerase or *Aspergillus nidulans* acetamidase and a *Trichoderma reseei* chbl promoter. As examples of suitable promoters for expression in a yeast species the Gal 1 and Gal 10 promoters of *Saccharomyces cerevisiae* can be mentioned.

The vector comprising the DNA fragment encoding the aspartic protease polypeptide may also comprise a selectable marker, e.g. a gene the product of which complements a defect in the host organism such as a mutation conferring an auxothrophic phenotype, or the marker may be one which confers antibiotic resistance or resistance to heavy metal ions.

In one specific embodiment, the expression vector is derived from pGAMpR as described in Ward et al., 1990 by substituting the coding sequence of that vector for bovine prochymosin with a coding sequence for the aspartic protease as defied above. An example of such a pGAMpR-derived expression vector is pGAMpR-C deposited in an *Aspergillus niger* var. *awamori* host environment under the accession Nos. CBS 108915 and CBS 108916, respectively.

In a subsequent step of the method a suitable host cell is transformed with the expression vector. The host cell may be transformed with an autonomously replicating vector or a vector that permits that the polypeptide becomes integrated into the host cell chromosome. Such integration is generally considered to be advantageous as the polypeptide is more likely to be stably maintained in the cell. Integration of the polypeptide into the host chromosome may be carried out according to conventional methods such as e.g. by homologous or heterologous recombination or by means of a transposable element.

In accordance with the invention, the host organism may be a cell of a higher organism such as an animal cell, including a mammal, an avian or an insect cell, or a plant cell. In useful embodiments the host organism may be a yeast species or a filamentous fungus species.

A suitable yeast host organism may advantageously be selected from a species of *Saccharomyces* including *Saccharomyces cerevisiae* or a species belonging to *Schizosaccharomyces*. Further useful yeast host organisms include *Pichia* spp. such as methylotrophic species hereof, including *Pichia pastoris*, and *Klyuveromyces* spp. including *Klyueromyces lactis*.

In a preferred embodiment, the host cell is a filamentous fungal cell. "Filamentous fungi" includes all filamentous forms of the subdivision Eumycota and Oomycota (as defined by Hawksworth et al., 1995, supra). The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. In a more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium*, and *Trichoderma* or a teleomorph or synonym thereof. In an even more preferred embodiment, the filamentous fungal host cell is an *Aspergillus* cell. In another still more preferred embodiment, the filamentous fungal host cell is an *Acremonium* cell. In another even more preferred embodiment, the filamentous fungal host cell is a *Fusarium* cell. In another even more preferred embodiment, the filamentous fungal host cell is a *Humicola* cell. In another even more preferred embodiment, the filamentous fungal host cell is a *Mucor* cell. In another even more preferred embodiment, the filamentous fungal host cell is a *Myceliophthora* cell. In another even more preferred embodiment, the filamentous fungal host cell is a *Neurospora* cell. In another even more preferred embodiment, the filamentous fungal host cell is a *Penicillium* cell. In another even more preferred embodiment, the filamentous fungal host cell is a *Thielavia* cell. In another even more preferred embodiment, the filamentous fungal host cell is a *Tolypocladium* cell. In another even more preferred embodiment, the filamentous fungal host cell is a *Trichoderma* cell. In a most preferred embodiment, the filamentous fungal host cell is an *Aspergillus awamori, Aspergillus foetidus, Aspergillus nidulans, Aspergillus japonicus, Aspergillus niger* (including *Aspergillus nigar* var. *awamori*) or *Aspergillus oryzae* cell. In another most preferred embodiment, the filamentous fungal host cell is a *Fusarium* cell of the section Discolor (also known as the section Fusarium). In another preferred embodiment, the filamentous fungal parent cell is a *Fusarium* strain of the section Elegans, e.g., *Fusarium oxysporum*. In another most preferred embodiment, the filamentous fungal host cell is a *Humicola insolens* or *Thermomyces lanuginosa* cell. In another most preferred embodiment, the filamentous fungal host cell is a *Rhizomucormiehei* cell. In another most preferred embodiment, the filamentous fungal host cell is a *Myceliophthora thermophilum* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the *Trichoderma* cell is a *Trichoderma harzianum, Trichoderma reseei, Trichoderma koningii, Trichoderma longibrachiatum, Trichoderma reesei* or *Trichoderma viride* cell.

Some of the above useful host organisms, such as fungal species, may be transformed by a process which involves protoplast formation and transformation of the protoplasts followed by regeneration of the cell wall in a manner known by a person of skill.

In subsequent steps the thus transformed host cell is cultivated under conditions where the polypeptide is expressed, and the aspartic protease is harvested. The medium used to cultivate the transformed host cells may be any conventional medium suitable for growing the host cells in question and obtaining expression of the polypeptide. Suitable media are available from commercial suppliers or can be prepared according to published recipes.

The resulting aspartic protease is typically recovered from the cultivation medium by conventional procedures including separating the host cells from the medium by centrifugation or filtration, if necessary, after disruption of the cells, followed by precipitating the proteinaceous components of the supernatant or filtrate e.g. by adding a salt such as ammonium sulphate, followed by a purification step. Alternatively, the cell-free cultivation medium may also, optionally after concentrating or diluting it or addition of conventional additives, be used directly as a coagulant product for cheese manufacturing.

In accordance with the invention, the above method is preferably a method wherein the yield of aspartic protease is at least 2%, 5%, 10%, 25%, 50%, 100% or 200% higher than the yield of a non-modified polypeptide comprising an aspartic protease obtained when, under identical production conditions, using the same host. As mentioned above, the aspartic protease is preferable a mammalian chymosin, such as preprochymosin, prochymosin or chymosin.

In a further preferred embodiment, the method is one wherein the yield of chymosin milk-clotting activity in terms of arbitrary units of cultivation medium is increased by at least 25% relative to the yield obtained using, under identical cultivation conditions, a production strain that is identical to that of the transformed host organism except that it expresses a polypeptide comprising a mammalian chymosin molecule that has not been modified to comprise at least one —N—X-T-glycosylation site. However, the yield of chymosin milk-clotting activity in terms of arbitrary units of cultivation medium is preferable increased by at least 50%, such as at least 75% including at least 100%.

In a still further aspect there is provided a milk clotting composition comprising the polypeptide comprising an aspartic protease including a mammalian chymosin as defined herein and a pepsin and produced by the above method including such a prochymosin or chymosin that is in a substantially deglycosylated form. Such a composition may, in addition to the active milk-clotting enzyme, comprise additives that are conventionally used in rennets of animal origin such as e.g. NaCl.

The recombinant milk clotting composition as provided herein is useful as a milk coagulant product. Accordingly, an important objective of the invention is to provide a method of manufacturing cheese, comprising adding a milk clotting effective amount of the above composition to milk and carrying out appropriate further cheese manufacturing steps. The polypeptide comprising a mammalian chymosin of the invention is suitable for cheese manufacturing processes wherein the milk is selected from cow's milk, camel milk, buffalo milk, goat's milk and sheep's milk.

In useful embodiments, the milk clotting composition containing the polypeptide comprises on the one hand a mammalian chymosin as defined above and on the other hand at least one further milk clotting enzyme. The at least two milk clotting enzymes included in said composition will also in useful embodiments of the invention have a milk dotting activity ratio, which lie within a range of 1:99 to 99:1, in addition to being characterized by the finding that at least 2% of its milk clotting activity originates from the mammalian chymosin as defined above such as e.g. at least 5%, 10%, 20%, 50%, 75, 90 or 98% of the activity.

In a preferred embodiment, the composition according to the invention is capable of retaining at least 50% of its initial milk clotting activity at a temperature of −20° C. or higher for 1 week or more. It is, however, in further embodiments preferred that the composition retains at least 60% of its initial metabolic activity, e.g. at least 70% including at least 80% such as at least 90% of its initial metabolic activity.

There is also provided a method of manufacturing cheese from milk including cow's milk, comprising adding a milk clotting effective amount of the polypeptide as defined herein or of the above composition and carrying out appropriate further cheese manufacturing steps.

As described above it is believed that the present inventors have identified a novel concept to improve production of aspartic protease. Without being limited to theory, it is believed that the disclosed concept could also be used on other enzymes. Accordingly, the term "aspartic protease" as described herein in relation to aspects and preferred embodiments of the invention may be any enzyme in general. Preferred enzymes are a lipase, an amylase, a phospholipase, a subtilisin protease, or a cellulase.

The invention will now be explained in further details in the following examples and the drawings wherein FIG. 1 A schematically illustration of a fusion protein comprising a fusion partner and an aspartic protease amino acid sequence. The aspartic protease amino acid sequence comprises an artificial linker.

FIG. 2 shows the nucleotide sequence of modB-XS (modified SalI/XbaI fragment) with a number of unique restriction sites (SEQ ID NO:2). See example 1.

FIG. 3: Synthetic DNA fragments further described in example 1 (SEQ ID NO:3-SEQ ID NO:8).

EXAMPLES

Example 1

Construction of a Novel Plasmid Encoding Bovine Chymosin B with an Optimised Glycosylation Site 1.1 Introduction In one currently used method of producing bovine chymosin recombinantly in an *Aspergillus* host strain, chymosin B is produced as a fusion protein between *Aspergillus* glucoamylase and prochymosin B (Ward et al. 1990). For this purpose the gene sequences encoding *Aspergillus* glucoamylase and prochymosin B were fused.

In this example the prochymosin B gene sequence is replaced by a new, synthetic chymosin B gene that comprises one optimised N-glycosylation site. The new gene was called chymosin modBM. In order to construct the chymosin modBM gene a synthetic gene was designed encoding the chymosin modBM gene. As a control a synthetic gene was designed encoding the native chymosin B gene. Both synthetic genes had a codon usage optimised for expression in *Aspergillus* and were expressed as fusion proteins with glucoamylase.

1.2. Materials and Methods 1.2.1 Construction of a Modified Chymosin B Encoding Gene A synthetic DNA fragment of 1138 bp was designed and designated modB-XS (FIG. 2). Fragment modB-XS comprises a unique SalI and XhoI site for cloning purposes. This fragment comprises the information for prochymosin B. The prochymosin B encoding part of modB-XS is designated chymosin modB. A second synthetic fragment was designed and designated modBM-XS. ModBM-XS is identical to modB-XS, except for the introduction of one additional glycosylation site (S293T, resulting in a N—H-T glycosylation site).

1.2.2 Construction of Plasmids Encoding Bovine Chymosin B

Five synthetic DNA fragments were made, using synthetic oligonucleotides. The process of combineing oligonucleotides into a larger DNA fragment by annealing is well known by the skilled artisan.

The five fragments obtained were (see FIG. 3):
(i) a 410 bp SalI-SphII I fragment (SEQ ID NO:3)
(ii) a 220 bp SphI-BsrGI fragment (SEQ ID NO:4)
(iii) a 190 bp BsrGI-KpnI fragment (SEQ ID NO:5)
(iv) a 320 bp KpnI-XbaI fragment (SEQ ID NO:6)

For construction of the modBM gene a modified KpnI-XbaI fragment was designed (SEQ ID NO:7).

All sub fragments were cloned in vector pCRII-TOPO (Invifrogen) according to the instructions supplied by the manufacturer.

For combining the sub-fragments, a vector was created with an optimized polylinker (SalI-SphI-BsrGI-KpnI-XbaI).

For this purpose a synthetic polylinker (SEQ ID NO:8) was designed and cloned into the pCRII-TOPO vector. Later polylinker fragment was inserted in the BssHI sites of plasmid pBluescript SK II, resulting in pSK-MCS.

The above subfragments were isolated from the pCRII-Topo vectors and sequentially cloned into pSK-MCS. The final vectors were designated respectively pSKMCS-SaI-Xba-B (chymosin B) and pSKMCS-SaI-Xba-BM (chymosin BM).

The expression cassette from pGAMpR (Ward et al. 1990) was isolated as a SpeI-XbaI fragment. The SalI site of pBluescript SKII+ was deleted, resulting in pSK-SaI-. The expression cassette was cloned into the SpeI-XbaI sites from pSK-SalI, reuslting in plasmid SK-Sal-GlaChy. The SalI-XbaI fragments of pSKMCS-Sal-Xba-B and pSKMCS-Sal-Xba-BM, respectively, were used to replace the SalI-XbaI fragment in pSK-Sal-GlaChy, resulting in plasmids pSKMod-ChymB and pSKModChymBM, respectively.

The SpeI-XbaI fragments of the pSKModChym constructs were used to replace the SpeI-XbaI fragments in pGAMpR, resulting in pGAMmodB and pGAMmodBM, respectively. Thus, the pGAMmodB and pGAMmodBM constructs comprise a gene encoding native chymosin and a modified chymosin (S293T), respectively.

Example 2

Production of Chymosin Using an *Aspergillus niger* var. *awamori* Strain Transformed with pGAMmodBM 2.1 Introduction To investigate the effect of improved glycosylation on chymosin production in fungi, *Aspergillus* was transformed with the new expression plasmid pGAMmodBM. As a control, transformants were generated with pGAMmodB as well.

2.2 Transformation of the *Aspergillus niger* var. *awamori* Strain with pGAMmodBM and pGAMmodB A derivative of *Aspergillus niger* var. *awamori*, strain GCI-HF1-2dgr246, was used as recipient. Strain GCI-HF1-2dgr246 comprises several copies of the pGAMpR plasmid. A derivative strain, dgr246pyrG (Ward et al.1990) was made by curing all copies of pGAMpR by means of selecting for a pyrG phenotype, rendering the strain incapable of growing in the absence of uridine.

The dgr246pyrG strain was deposited under the Budapest Treaty with the Centraalbureau voor Schimmelcultures (CBS), Oosterstraat 1, P.O. Box 273, 3740 AG Baarn, The Netherlands, on 13 Jun. 2000 under the accession No. CBS 108914.

2.2.1. Propagation of Fungal Biomass 50 ml of CSL medium [per liter: corn steep liquor, 100 g; $NaH_2PO_4.2H_2O$, 1 g; $MgSO_4$, , 0.5 g; Mazu antifoaming agent, 2 g, maltose, 100 g, glucose, 10 g, fructose, 50 g, water 736.5 g] was added to a sterile 250 ml flask, 0.5 ml penicillin/streptomycin supplement (Gibco-BRL #15140-114)] was added and the medium inoculated with $10^6$ spores per ml. The inoculated medium was cultivated overnight at 34-37° C. at 200-250 rpm to obtain a dense suspension of mycelium. 10 ml of this pre-culture was transferred to 100 ml complete Aspergillus medium in a 500 ml flask without baffles and incubated overnight at a temperature of 34-37° C. at 200-250 rpm to obtain a mycelial biomass.

2.2.2. Generation of Protoplasts

Mycelium as obtained in the above step was filtered over sterile myracloth, washed with sterile water and subsequently washed with 1700 mOsmol $NaCl/CaCl_2$ (0.27 M $CaCl_2.2H_2O$, 39.7 g/l; 0.58 M NaCl, 33.9 g/l), gently squeezed dry and transferred to a Falcon tube to determine the weight and kept on ice.

20 ml 1700 mOsmol $NaCl/CaCl_2$ per g mycelium was added in order to resuspend the mycelium followed by adding 50 mg Sigma L-1412 Trichoderma harzianum Lytic Enzyme per g mycelium dissolved in a small volume of 1700 mOsmol $NaCl/CaCl_2$, and incubated in an Erlenmeyer flask at 100 rpm, 37° C. for about 4 hrs during which period the mycelium was repeatedly resuspended every 30 minutes.

After thorough protoplasting was obtained, i.e. many free protoplasts occur and with hardly any intact mycelium left, the mixture was filtered on ice, using Mesh sheet or myracloth and an equal volume of ice cold STC1700 (1.2 M sorbitol, 218 g/l; 35 mM NaCl, 2.04 g/l; 10 mM Tris.HCl pH 7.5 and 50 mM $CaCl_2.2 H_2O$, 7.35 g/l) was added. The number of protoplasts was counted using a glass Bürger-Türk chamber. The protoplast suspension was spun using a bench top centrifuge at 2,000 rpm at 4° C. The resulting pellet was resuspended very gently in 20 ml ice cold STC1700. This washing procedure was repeated twice and the final pellet was resuspended in ice cold STC1700 to a final concentration of about $1×10^8$ protoplasts per ml followed by adjustment to $1×10^8$ protoplasts per ml.

2.2.3. Transformation

200 μl $2×10^7$ protoplasts, 2 μl of 0.5 M ATA (0.5 M aurine carboxylic acid (Sigma) in 20% 5 ethanol) and DNA (comprising a marker) up till 15 μl, typically 5-10 μg of DNA, were mixed in a 12 ml test tube. As control a corresponding mixture, but without DNA was used. The transformation mixtures were incubated on ice for 25 minutes followed by adding a first drop of 250 μl PTC (60% PEG 4000; 10 mM Tris.HCl pH 7.5; 50 mM $CaCl_2$) by tipping the tube several times without allowing the mixture touch the lid and subsequently a second drop of 250 μl of PTC was added, mixed and 850 μl was added followed by mixing. Each tube was incubated at room temperature exactly 20 minutes followed by filling the tubes with chilled STC1700 and mixing the suspension by reverting the tubes. The mixture was centrifuged for 8-10 min. using a bench top centrifuge at 2000 rpm at 4° C. The resulting pellet was dissolved gently in about 400-800 μl STC1700.

2.2.4. Regeneration and Selection of Transformants

The transformation mixture was spread onto solid selective regeneration medium plates containing per liter medium: agar, 15 g; sorbitol, 218 g; AspA salts 50× (per liter: 300 g $NaNO_3$, 26 g KCl, 76 g $KH_2PO_4$, 18 ml 10 M KOH, pH about 6.5); glucose 50%, 20 ml; Gibco-BRL #15140-114 Pen-Strep, 10 ml; $MgSO_4$, 2 ml; trace elements (2.2 g $ZnSO_4$, 1.1 g $H_3BO_3$, 0.5 g $MnCl_2.7H_2O$, 0.5 g $FeSO_4.7H_2O$, 0.17 g $CoCl_2.6H_2O$, 0.16 $CuSO_4.5H_2O$, 0.15 $NaMoO_4.2H_2O$, 5 g EDTA, water to 100 ml, pH 6.5), 1 ml. The plates were incubated at 37° C. for 5-10 days and transformants selected.

2.3. Small Scale Shake Flask Production of Chymosin Using Aspergillus niger var. awamori Transformed with pGAMmodBM 75 of the above transformants were selected. As controls the above described strain CBS108914, which does not produce chymosin, and the Aspergillus niger var. awamori chymosin production strain dgr246chlor25 (Dunn-Coleman et al. 1991) was used which in the following also is referred to as PIM1149.

An appropriate amount of the transformants and the control strains were used for inoculation of 20 ml CSL medium [per liter: corn steep liquor, 100 g, $NaH_2PO_4.2H_2O$, 1 g; $MgSO_4$, 0.5 g; Mazu antifoaming agent, 2 g; maltose, 100 g; glucose, 10 g; fructose, 50 g; water, 736.5 g]. Following 24-48 hours of growth at 37° C. and 200 rpm, 2 ml of this preculture was used for inoculation of 20 ml complete Aspergillus induction medium. The respective strains were cultivated for 10 days at 37° C. and 200 rpm and samples were collected at day 6 and day 8. Samples were centrifuged at 14,000 rpm in an Eppendorf centrifuge and clear supernatant was separated and stored at −20° C. prior to determining the milk clotting activity using a conventional assay.

The results of this study are summarized in Table 1.

TABLE 1

Summarises the results of chymosin production shake flask experiments with 20 selected pGAMmodBM transformants of Aspergillus niger var. awamori (out of 75) using as a positive control a strain of Aspergillus niger var. awamori carrying pGAMpR (PIM1149) and as the negative control an Aspergillus niger var. awamori cured of plasmids encoding chymosin. Arbitrary milk clotting units (AU) were determined after 8 days incubation.

| transformant nr. | AU day 8 |
|---|---|
| 1 (BM27) | 217 |
| 2 | 155 |
| 3 | 100 |
| 4 | 166 |
| 5 | 198 |
| 6 | 179 |
| 7 | 122 |
| 8 | 157 |
| 9 | 169 |
| 10 | 129 |
| 11 | 157 |
| 12 | 116 |
| 13 | 52 |
| 14 | 48 |
| 15 | 138 |
| 16 | 116 |
| 17 | 116 |
| 18 | 100 |
| 19 | 95 |
| 20 | 78 |
| PIM | 100 |
| Cured | <2.5 |

It appears that after 8 days of cultivation, the PIM1149 control strain had produced 100 AU. Three of the tested pGAMmodBM transformed strains produced in excess of 170 AU of which the highest producing strain designated BM27 produced 217 AU, i.e. more than two times higher yield of milk clotting activity than that obtained with the control strain. A further 6 transformants showed chymosin production level more than 25% higher than that of the PIM1149 strain. In total, 12% of the tested transformants showed significantly higher production levels of milk clotting activity than did the positive control strain.

Relative glycosylation was increased in both high and low producing transformants. In fermentations of the PIM1149 control strain, about 10% of the chymosin molecules were glycosylated whereas in pGAMmodBM transformants more than 90% of the molecules were glycosylated.

2.4 Laboratory Scale Fermentation of the PGAMmodBM Transformant BM27

Two independent laboratory scale fermentations (A and B) were carried out with the BM27 transformant and, as a positive control, an *Aspergillus niger* var. *awamori* strain carrying the pGAMpR construct using a 2 l fermentor. The fermentation medium used had the following composition: Soy meal Danpro H supplied by Central Soya, 562.6 g; $NH_4SO_4$, 2,065.5 g; $NaH_2PO_4$, 25 g, $MgSO_4$, 12.5 g; Tween 80, 12.5 g; Mazu DF antifoaming agent, 37.5; tap water, 9,625 g; condensate (water) 2,000 g; sugar solution consisting of maltose (Glucidex 47 supplied by Roquette), 5,000 g and tap water, 7,500 g.

The maltose solution was autoclaved separately at 121° C. for 20 minutes. 3,300 g of the solution was added to the fermentor after heat treatment and the remaining 9,200 g was to be pumped into the fermentor during operation.

The fermentation conditions were 37° C. at pH 5.5. The fermentor was inoculated with 50 ml of pre-culture prepared as described above by inoculating 100 ml of CSL medium in a 500 ml shake flask with $1\times10^8$ spores. The culture was grown overnight at 37° C. at 200 rpm for 140 hours. Samples were collected every 24 hours and assayed for milk clotting activity of chymosin.

The results are summarized in Table 2.

TABLE 2

Illustrates the results of a laboratory scale fermentation experiment using a selected pGAMmodBM transformant of *Aspergillus niger* var. awamori, modBM#27 and as a positive control a strain of *Aspergillus niger* var. awamori carrying pGAMpR (PIM2075). Arbitrary milk clotting activities were determined after 70, 95 119 and 140 hrs of fermentation. The PIM B culture was discarded after ± 135 hours.

|        | 70 hrs | 95 hrs | 119 hrs | 140 hrs |
| --- | --- | --- | --- | --- |
| PIM A  | 71  | 310 | 309 | 308 |
| PIM B  | 57  | 228 | 333 | n.d. |
| BM27 A | 58  | 229 | 529 | 687 |
| BM27 B | 107 | 419 | 572 | 695 |

As it appears, the level of milk clotting activity produced by the BM27 transformant was after 140 hours of fermentation about 2-fold higher than that of the control strain PIM2075. It can also be observed that whereas the control strain reached a maximum level after 119 hours, the BM27 strain continued to produce chymosin after this point in time.

The high levels of milk clotting activity were obtained with the BM27 strain without deglycosylation of the samples. More than 90% of the chymosin produced by BM27 was glycosylated. From these results it becomes clear that glycosylation was an important factor for an effective production of chymosin by *Aspergillus* strains. With the location of the introduced modified glycosylation site at position 291, according to the chymosin numbering (Gilliland, 1990) which might block the catalytic cleft of the chymosin molecule, the possibility might be considered that the improved activity of chymosin BM was partly caused by a reduced autocatalytic activity. The observed increased glycosylation does probably improves the secretion of the enzyme and probably also results in an increased protein stability, possibly conferring to glycosylated chymosin.

Example 3

Use of a Glycosylated Linker to Increase Protein Secretion by *Aspergillus niger*

3.1 Introduction

The general practice for production of non-homologous proteins in fungi is to make a fusion of the protein of interest to a highly secreted fungal carrier molecule such as glucoamylases, amylases, cellulases etc. A specific cleavage site is usually introduced between he carrier molecule and the non-fungal protein. One example of such a production system is the production of chymosin by *Aspergillus niger*. In this case the chymosin gene is fused to the fungal carrier glucoamylase.

As shown in Example 2, chymosin production levels by *Aspergillus* can be strongly increased by introducing an N-glycosylation site in the protein of interest, even though the fungal carrier molecule is heavily glycosylated. Due to the introduction of an additional N-glycosylation site, the resulting protein molecule will differ from the native molecule by one or more amino acids. However, for public acceptance of such an enzyme for food applications it is desirable to produce an enzyme that is identical to the natural enzyme.

To obtain increased production yields while producing a nature-identical enzyme a new strategy was designed. In this strategy an artificial linker-sequence was introduced between the gene encoding the carrier molecule glucoamylase and the gene encoding the protein of interest. This linker was designed to contain an additional N-glycosylation site, N—X-T, which is the preferred eukaryotic N-glycosylation recognition site. In this way the fusion protein will be more heavily glycosylated and will thus be produced at higher levels by the fungus. The protein of interest is released from the carrier protein by specific cleavage during secretion or in the culture medium. This specific cleavage should occur at the C-terminal from the linker sequence to obtain a nature identical protein.

To study this, a new DNA construct was designed for chymosin production, called pGAMmodB2. A linker sequence, encoding the amino acids T-D-N—S-T, was introduced between the carrier molecule glucoamylase and bovine chymosin. During a so-called activation step (incubation at low pH) mature chymosin is produced from prochymosin by autocatalytical cleavage, resulting in removal of the pro-part of prochymosin. Chymosin produced by pGAMmodB2 transformants using this strategy is completely identical to the natural chymosin. Chymosin production in fungi with plasmids pGAMpR (direct fusion between glucoamylase and chymosin) and pGAMmodB2 is schemetically shown in Table 3.

TABLE 3

Shows the chymosin production in shake flask by transformants of plasmids pGAM-modB2. Arbitrary milk clotting units were determined after 8 days Incubation.

| transformant | AU |
| --- | --- |
| PIM1 | 68 |
| PIM2 | 67 |
| cured | 0 |
| 1 | 0 |
| 2 | 21 |
| 3 | 0 |
| 4 | 0 |
| 5 | 26 |
| 6 | 36 |
| 7 | 135 |
| 8 | 78 |
| 9 | 0 |
| 10 | 22 |
| 11 | 24 |
| 12 | 0 |
| 13 | 56 |
| 14 | 22 |
| 15 | 0 |
| 16 | 0 |
| 17 | 0 |
| 18 | 0 |
| 19 | 28 |
| 20 | 0 |
| 21 | 0 |
| 22 | 29 |
| 23 | 29 |
| 25 | 0 |
| 26 | 0 |
| 27 | 32 |
| 28 | 24 |
| 29 | 28 |
| 30 | 0 |
| 32 | 0 |
| 33 | 33 |
| 35 | 0 |
| 36 | 0 |
| 37 | 0 |
| 38 | 22 |
| 39 | 0 |
| 40 | 0 |
| 41 | 0 |
| 42 | 59 |
| 43 | 0 |
| 44 | 17 |
| 46 | 0 |
| 47 | 0 |
| 48 | 0 |
| 49 | 0 |
| 50 | 0 |
| 51 | 0 |
| 52 | 0 |
| 53 | 22 |
| 54 | 0 |
| 56 | 0 |
| 58 | 0 |
| 63 | 0 |
| 65 | 44 |
| 67 | 0 |
| 68 | 67 |
| 70 | 21 |
| 78 | 0 |
| 80 | 0 |
| 82 | 0 |
| 83 | 36 |
| 85 | 88 |
| 86 | 47 |
| 87 | 49 |
| 88 | 17 |
| 89 | 0 |
| 90 | 21 |
| 91 | 21 |
| 92 | 85 |
| 93 | 45 |

3.2 Construction of Plasmid pGAMmodB2

For construction of pGAMmodB2 the XhoI site in the pBluescript vector was removed by digesting pBluescript SKII+ (Stratagene) with XhoI and SalI and subsequently re-ligating the vector. The chymosin gene was cloned from plasmid pGAMmodB (see Example 1) into this vector as a SpeI-XbaI fragment, resulting in pLinker1. A small PCR fragment containing the linker sequence was generated using oligonucleotides 8081 (5' CATGTACACGCTGAACA-GATCCTGAGC (SEQ ID NO:9) and GlyLin1 (5' CGT CGA CCG CTA CGG TGA CTG ACA CCT GGC GTA CCG ACA ACT CCA CCG AGA TCA CTC GCA TCC CCC TCT ACA AG (SEQ ID NO:10)).

The resulting PCR fragment was cloned in the pCR2.1-Topo vector (Invitrogen) according to the instructions supplied by the manufacturer, and the DNA sequence was confirmed. Subsequently, the PCR fragment was cloned as a SalI-XhoI fragment in the corresponding sites of pLinker1, resulting in vector pLinker-TDNST. To construct the final vector, pGAMmodB2, the chymosin expression cassette was isolated from pLinker-TDNST as a 4.4 kb XbaI-SpeI fragment and ligated with the 9 kb XbaI-SpeI vector-fragment from pGAMmodB.

3.3 Transformation of CBS108914

Generation of Protoplasts of Strain CBS108914

Strain CBS108914 was transformed with plasmid pGAM-modB2 using an optimized procedure. Strain CBS108914 was inoculated in 20 ml CSL medium (Corn Steep Liquor 100 g/l, $NaH_2PO_4.H_2O$ 1 g/l, $MgSO_4$ 0,5 g/l, Mazu antifoam 2 g/l, Maltose 100 g/l, Glucos 10 g/l, Fructose 50 g/l, pH 5.8) and incubated overnight at 37° C. at 200-250 rpm. 10 ml of the pre-culture was transferred to 100 ml complete *Aspergillus* medium (10 g/l glucose, 6 g/l $NaNO_3$, 0,52 g/l KCl, 1,52 g/l $KH_2PO_4$, 0.36 ml 10M KOH, 2 g/l uridin, 20 mM $NaNO_2$, 2 mM $MgSO_4$, 2 mg/l Thiamin, 2 mg/l Riboflavin, 2 mg/l nicotinamide, 1 mg/l pyridoxine, 0.2 mg/l panthothenic acid, 4 μg/l biotin, 2.2 mg/l $ZnSO_4$, 1.1 mg/l $H_3BO_3$, 0.5 mg/l $MnCl_2.4H_2O$, 0.5 mg/l $FeSO_4.7H_2O$, 0.17 mg/l $CoCl_2.6H_2O$, 0.16 mg/l $CuSO_4.5H_2O$, 0.15 mg/l $Na_2MoO_4.2H_2O$, 5.0 mg/l EDTA) in a 500 ml flask without baffles. This culture was incubated overnight at 37° C. and 200-250 rpm. The mycelium was filtered over a sterile piece of myracloth (Calbiochem) and washed once with sterile water and once with 1700 mosmol $NaCl/CaCl_2$ (0.27 M $CaCl_2.2H_2O$, 0.58 M NaCl). The mycelium was transferred to a sterile flask and resuspended in 20 ml 1700 mosmol $NaCl/CaCl_2$ per gram mycelium. 50 mg Lytic Enzyme (Sigma) was added per gram mycelium. The protoplasting reaction was incubated at 100 rpm and 37° C. until ready (many free protoplasts). The mixture was filtered on ice using myracloth. An equal volume of ice cold STC1700 (1.2 M Sorbitol, 35 mM NaCl, 10 mM Tris.HCl pH 7.5, 50 mM $CaCl_2.2H_2O$) was added. The protoplasts were collected by centrifugation 10 min in bench top centrifuge at 2000 rpm at 4° C. The pellet was resuspended in 20 ml ice cold STC1700 and protoplasts were collected again by centrifugation for 10 min in a bench top centrifuge at 2000 rpm at 4° C. This wash step was repeated once. The final protoplast pellet was dissolved in ice cold STC1700 to a final concentration of $10 \times 10^8$ protoplast/ml.

Transformation of strain CBS108914

$2.10 \times 10^7$ protoplasts were mixed with 2 μl of ATA (0.5 M Aurinetricarboxylic Acid (Sigma) in 20% Ethanol) and 10 μg pGAMmodB2 DNA. This was incubated on ice for 25 minutes. 1350 μl PTC (60% PEG 4000, 10 mM Tris.HCl pH 7.5, 50 mM $CaCl_2$) was added in small drops and mixed well. The tube was incubated at room temperature. After exactly 20 minutes the tube was filled with chilled STC1700 and mixed immediately by reversing the tube. The protoplasts were collected by centrifugation for 10 minutes in a bench top centrifuge at 2000 rpm at 4° C. The pellet was dissolved in 500 ul STC1700. This was spread on selective regeneration plates (218 g/l sorbitol, 10 g/l glucose, 6 g/l $NaNO_3$, 0,52 g/l KCl, 1,52 g/l $KH_2PO_4$, 0.36 ml 10M KOH, 2 g/l uridin, 15 g/l agar, 2.2 mg/l $ZnSO_4$, 1.1 mg/l $H_3BO_3$, 0.5 mg/l $MnCl_2.4H_2O$, 0.5 mg/l $FeSO_4.7H_2O$, 0.17 mg/l $CoCl_2.6H_2O$, 0.16 mg/l $CuSO_4.5H_2O$, 0.15 mg/l $Na_2MoO_4.2H_2O$, 5.0 mg/l EDTA). Plates were incubated at 35° C. for 10 days.

Approximately 70 transformants were purified on selective minimal medium plates (identical to selective regeneration plates but without sorbitol) and single colonies were used to inoculate PDA plates (potato dextrose agar, Oxoid). Spores were isolated and stored in 20% glycerol at −80° C.

3.4 Analysis of Transformants

Spores of transformants were used to inoculate 20 ml of CSL medium in 50 ml Erlenmeyer shake flasks. Shake flasks were incubated 48 hrs at 37° C. and 200. 2 ml of the culture was transferred to 20 ml of Induction medium (150 g/l Maltose, 60 g/l Soybean Dan-Pro, 70 g/l Na-Citrate, 15 g/l Ammoniumsulphate, 1 g/l $NaH_2PO_4-H_2O$, 1 g/l $MgSO_4$, 1 ml/l Tween 80, 1 mg/l Arginine, pH 6.0) and the cultures were incubated at 37° C., 200 rpm during 8 days. 1 ml medium samples were taken at day 7 and day 8. Milk clotting activities were determined by measuring milk-clotting activities in 96 wells microtiter plates. The best producers were selected and screened in a third small scale shake flask experiment to confirm the results obtained. Chymosin production was tested in pilot scale fermentors with two selected transformants.

3.5 Protein Analysis

The N-terminal sequence of the resulting chymosin was determined and was found to be identical to the natural chymosin and to the chymosin produced in *Aspergillus* with the pGAMpR expression construct.

3.6 Results

After 180 hrs the best pGAMmodB2 transformants were found to produce over 20% more than a reference strain producing bovine chymosin (see Table 4 below). Autocatalytical cleavage of the glucoamylase-chymosin molecule resulted in a nature identical protein as was confirmed by N-terminal sequencing.

TABLE 4

Shows the production of chymosin by pGAMmodB2 transformants in pilot scale fermentations. Production levels are compared to production level by a comparable transformant of pGAMpR (PIM). Arbitrary milk clotting units were determined at different time points during the fermentation.

| hr  | modB2#7 | modB2#85a | modB2#85b | PIM |
|-----|---------|-----------|-----------|-----|
| 0   | 0       | 0         | 0         | 0   |
| 28  | 0       | 0         | 0         | 0   |
| 52  | 0       | 3         | 0         | 0   |
| 76  | 14      | 24        | 16        | 14  |
| 105 | 97      | 110       | 90        | 86  |
| 129 | 209     | 226       | 153       | 181 |
| 146 | 274     | 295       | 264       | 262 |
| 169 | 347     | 376       | 345       | 316 |
| 191 | 383     | 426       | 390       | 353 |

These results show that introduction of a glycosylated linker sequence between a fungal carrier molecule and a non-fungal protein is an effective method for increasing protein production levels in fungi, even though the carrier molecule already is heavily glycosylated. This strategy does not require any amino acid sequence change in the enzyme of interest, making it an especially useful tool for production of enzymes for use in human and animal food.

Example 4

Comparison of the Activity of the Chymosin BM Before and After Deglycosylation

4.1 Introduction

In Example 2, the development of the new Aspergillus strain producing a chymosin BM (S293T) was described. This strain produces more glycosylated chymosin BM than the strain would produce native calf chymosin. In this Example the glycan moiety effect on chymosin BM (S293T) activity is studied and compared with the activity of native calf chymosin.

4.2 Material and Methods

The activities of calf chymosin and the chymosin BM (S293T) were determined before and after deglycosylation with endoglycosidase H (Rec. *E. Coli*, Boehringer, Mannheim, Germany).

Purified samples were adjusted to 200 IMCU/ml with 80 mM acetate buffer pH 5.5 and 3 ml samples containing 600 IMCU and 0.15 U Endoglycosidase H were incubated over night at room temperature. As a control, the enzyme was substituted by acetate buffer and also included. Activity measurements were performed using the Remcat Strength Analytical Method International IDF standard 157A: 1997.

SDS-Page (Nupage Bis-Tris 4-12% mes buffer Novex, Calif.) was used to determined the glycosylation levels of the enzymes.

4.3 Results

Comparison of chymosin BM and calf chymosin on SDS Page before deglycosylation reveal significant differences in glycosylation levels. The chymosin BM showed significant increased glycosylation.

As shown in the below Table 5, the glycosylation of the enzyme had a significant inhibitory effect on the milk clotting activity of chymosin BM since the milk clotting activity increased to 32% of the initial activity when the chymosin BM was deglycosylated by Endoglucosidase H. For calf chymosin only little or no effect was found since the increase of activity is insignificant.

TABLE 5

Milk clotting activities of calf chymosin and chymosin BM before and after deglycosylation with Endglucosidase H

| Sample | Activity | n of samples | increase of activity by deglycosylation |
|---|---|---|---|
| Chymosin BM | | | |
| Glycosylated | 217 IMCU/ml | 3 | |
| Deglycosylated | 287 IMCU/ml | 3 | 32% |
| Native Calf Chymosin | | | |
| Glycosylated | 216 IMCU/ml | 3 | |
| Deglycosylated | 222 IMCU/ml | 3 | 2% |

The 2% increase in activity upon deglycosylation of the native calf chymosin is within the standard deviation of the method.

REFERENCES

Berka, R. M., Kodama, K. H., Rey, M. W., Wilson, L. J. and Ward, M. 1991. The development of *Aspergillus niger* var. *awamori* as a host for the expression and secretion of heterologous gene products. Biochemical Society Transactions 19:681-685.

Dunn-Coleman, N. S., Bloebaum, P., Berka, R. M., Bodie, E., Robinson, N., Armstrong, G., Ward, M., Przetak, M., Carter, G. L., LaCost, R., Wilson, L. J., Kodoma, K. H., Baliu, E. F., Bower, B., Lamsa, M. and Heinsohn, H. 1991. Commercial levels of chymosin production by *Aspergillus*. Bio/Technology 9:976-980.

Gilliland, G. L., Winborne, E. L., Nachmann, J. and Wlodawer, A. 1990. The three-dimensional structure of recombinant bovine chymosin at 2.3 Å resolution. Proteins: Structure, Function, and Genetics 8:82-101.

Sagt, C. M., Kleizen, B., Verwaal, R., de Jong, M. D., Muller, W. H., Smits, A., Visser, C., Boonstra, J., Verkleij, A. J., and Verrips, C. T. 2000. Introduction of an N-glycosylation site increases secretion of heterologous proteins in yeasts. Appl Environ Microbiol. Nov 66(11):4940-4.

Ward, M., Wilson, L. J., Kodoma, K. H., Rey, M. W. and Berka, R. M. 1990. Improved production of chymosin in *Aspergillus* by expression of glycoamylase-chymosin. Bio/Technology 8:435-440.

Wallis, G. L. F., Swift, R. J., Hemming, F. W., Trinci, A. P. J., Peberdy, J. F. 1999. Glucoamylase overexpression and secretion in *aspergillus niger*: analysis of glycosylation. Biochimica et Biophysica Acta 1472, 576-586.

Harboe, M. H. 1998. Rhizomucor miehei aspartic proteinases having improved properties. Aspartic proteinases (ed. M. James), Plenum Press, NY.

Peberdy, J. F. 1994. Protein secretion in filamentous fungi—trying to understand a highly productive black box. TIBTECH, 12, 50-57.

The invention claimed is:

1. A process for producing an isolated polynucleotide sequence encoding a modified polypeptide comprising: i) modifying a polynucleotide sequence that comprises a DNA sequence encoding a polypeptide comprising an aspartic protease amino acid sequence to encode an extra polypeptide N—X-T glycosylation site in the aspartic protease amino acid sequence; and ii) isolating the polynucleotide sequence resulting from step (i) which isolated polynucleotide sequence encodes the modified polypeptide.

2. The process for producing an isolated polynucleotide sequence of claim 1, wherein the aspartic protease is a chymosin.

3. The process for producing an isolated polynucleotide sequence of claim 2, wherein the chymosin is a mammalian chymosin.

4. The process for producing an isolated polynucleotide sequence of claim 3, wherein the mammalian chymosin is bovine chymosin.

5. The process for producing an isolated polynucleotide sequence of claim 2, wherein the polypeptide comprising an aspartic protease amino acid sequence is selected from the group consisting of pre-prochymosin, prochymosin and mature chymosin.

6. The process for producing an isolated polynucleotide sequence of claim 1, wherein the modified polypeptide comprises, within the aspartic protease amino acid sequence, an artificial linker comprising a N-glycosylation site.

7. The process for producing an isolated polynucleotide sequence of claim 1, wherein the polypeptide comprising an aspartic protease amino acid sequence comprises a fusion protein wherein the aspartic protease amino acid sequence is connected to a fusion partner.

8. The process for producing an isolated polynucleotide sequence of claim 7, wherein the fusion partner is selected from the group consisting of glucoamylase, alpha-amylase, cellobiohydrolase and a part thereof.

9. The process for producing an isolated polynucleotide sequence of claim 6, wherein the polypeptide comprising a aspartic protease amino acid sequence comprises a fusion protein that comprises the aspartic protease amino acid sequence connected to a fusion partner, which fusion partner is selected from the group consisting of glucoamylase, alpha amylase, cellobiohydrolase and a part thereof, and wherein the artificial linker is situated between a pro-sequence and the fusion partner.

10. An isolated polynucleotide sequence encoding a modified polypeptide obtainable by the process of claim 1.

11. A method of producing a modified polypeptide exhibiting aspartic protease activity comprising the steps of cultivating a host organism comprising the isolated polynucleotide sequence of claim 10 so that said modified polypeptide is produced and isolating the produced modified polypeptide exhibiting aspartic protease activity.

12. The method of producing a modified polypeptide of claim 11, wherein the host organism is a yeast cell or a filamentous fungal cell.

13. The method of producing a modified polypeptide of claim 12, wherein the host organism is a filamentous fungal cell and the filamentous fungal cell is an *Aspergillus* cell.

14. The process for producing an isolated polynucleotide sequence of claim 6 wherein the N-glycosylation site is a N—X-T glycosylation site.

15. The method of producing a modified polypeptide of claim 13, wherein the *Aspergillus* cell is an *Aspergillus niger* cell or an *Aspergillus niger* var. *awamori* cell.

16. A process for producing an isolated polynucleotide sequence encoding a modified polypeptide comprising: i) modifying a polynucleotide sequence that comprises a DNA sequence encoding a polypeptide comprising an aspartic protease amino acid sequence to encode an extra polypeptide N—X-T glycosylation site in the aspartic protease amino acid sequence; and ii) isolating the polynucleotide sequence resulting from step (i) which isolated polynucleotide sequence encodes the modified polypeptide, wherein the modified polypeptide comprises at least one —N—X-T-site introduced at position 291-293 (with reference to SEQ ID NO: 1), according to the chymosin numbering.

17. The process for producing an isolated polynucleotide sequence of claim 16, wherein the modified polypeptide is modified by substituting $S_{293}$ with T (with reference to SEQ ID NO: 1), creating the at least one N—X-T glycosylation site.

18. An isolated polypeptide exhibiting aspartic protease activity comprising a N—X-T glycosylation site, wherein the aspartic protease is a chymosin.

19. The isolated polypeptide of claim 18, wherein the chymosin is a mammalian chymosin.

20. The isolated polypeptide of claim 19, wherein the mammalian chymosin is bovine chymosin.

21. An isolated polypeptide exhibiting aspartic protease activity comprising a N—X-T glycosylation site wherein the polypeptide comprises at least one —N X-T- site introduced at position 291-293 (with reference to SEQ ID NO: 1), according to the chymosin numbering.

22. The isolated polypeptide of claim 21, wherein the polypeptide comprises $T_{293}$ (with reference to SEQ ID NO: 1), creating a N—X-T glycosylation site.

* * * * *

SEQUENCE LISTING

```
<160> NUMBER OF SEQ ID NOS: 10

<210> SEQ ID NO 1
<211> LENGTH: 323
<212> TYPE: PRT
<213> ORGANISM: Bos taurus

<400> SEQUENCE: 1

Gly Glu Val Ala Ser Val Pro Leu Thr Asn Tyr Leu Asp Ser Gln Tyr
1               5                   10                  15

Phe Gly Lys Ile Tyr Leu Gly Thr Pro Pro Gln Glu Phe Thr Val Leu
            20                  25                  30

Phe Asp Thr Gly Ser Ser Asp Phe Trp Val Pro Ser Ile Tyr Cys Lys
        35                  40                  45

Ser Asn Ala Cys Lys Asn His Gln Arg Phe Asp Pro Arg Lys Ser Ser
    50                  55                  60

Thr Phe Gln Asn Leu Gly Lys Pro Leu Ser Ile His Tyr Gly Thr Gly
65                  70                  75                  80

Ser Met Gln Gly Ile Leu Gly Tyr Asp Thr Val Thr Val Ser Asn Ile
                85                  90                  95

Val Asp Ile Gln Gln Thr Val Gly Leu Ser Thr Gln Glu Pro Gly Asp
            100                 105                 110

Val Phe Thr Tyr Ala Glu Phe Asp Gly Ile Leu Gly Met Ala Tyr Pro
        115                 120                 125

Ser Leu Ala Ser Glu Tyr Ser Ile Pro Val Phe Asp Asn Met Met Asn
    130                 135                 140

Arg His Leu Val Ala Gln Asp Leu Phe Ser Val Tyr Met Asp Arg Asn
145                 150                 155                 160

Gly Gln Glu Ser Met Leu Thr Leu Gly Ala Ile Asp Pro Ser Tyr Tyr
                165                 170                 175

Thr Gly Ser Leu His Trp Val Pro Val Thr Val Gln Gln Tyr Trp Gln
            180                 185                 190

Phe Thr Val Asp Ser Val Thr Ile Ser Gly Val Val Val Ala Cys Glu
        195                 200                 205

Gly Gly Cys Gln Ala Ile Leu Asp Thr Gly Thr Ser Lys Leu Val Gly
    210                 215                 220
```

-continued

```
Pro Ser Ser Asp Ile Leu Asn Ile Gln Gln Ala Ile Gly Ala Thr Gln
225                 230                 235                 240

Asn Gln Tyr Gly Glu Phe Asp Ile Asp Cys Asp Asn Leu Ser Tyr Met
                245                 250                 255

Pro Thr Val Val Phe Glu Ile Asn Gly Lys Met Tyr Pro Leu Thr Pro
            260                 265                 270

Ser Ala Tyr Thr Ser Gln Asp Gln Gly Phe Cys Thr Ser Gly Phe Gln
        275                 280                 285

Ser Glu Asn His Ser Gln Lys Trp Ile Leu Gly Asp Val Phe Ile Arg
    290                 295                 300

Glu Tyr Tyr Ser Val Phe Asp Arg Ala Asn Asn Leu Val Gly Leu Ala
305                 310                 315                 320

Lys Ala Ile
```

<210> SEQ ID NO 2
<211> LENGTH: 1142
<212> TYPE: DNA
<213> ORGANISM: artificial
<220> FEATURE:
<223> OTHER INFORMATION: DNA fragment comprising a DNA fragment of 1138
      bp designed to comprise a N-H-T glycosylation site and unique SalI
      and XhoI sites for cloning purposes (modB-XS).

<400> SEQUENCE: 2

```
cggtcgaccg ctacggtgac tgacacctgg cgtgccgaga tcactcgcat cccctctac      60 aagggcaagt ctctgcgtaa ggctctcaag gagcacggtc tgctcgagga tttcctgcag    120
aagcagcagt acggcatcag ctctaagtac agcggtttcg gcgaggtggc cagcgtgcct    180
ctcactaact acctggacag ccagtacttc ggtaagatct accttggcac tcccctcag    240 gagttcaccg ttctgttcga tactggttcc agcgacttct gggttccctc catctactgt    300
aagagcaacg cttgcaagaa ccaccagcgc ttcgatcctc gcaagtccag caccttccag    360
aaccttggca gccccttc catccactac ggtactggca gcatgcaggg tatccttggc      420
tacgacaccg ttaccgtgtc caacatcgtc gatattcagc agaccgtggg tctgagcacc    480
caggagcctg gcgatgtctt cacttacgcc gagttcgatg gtatcctcgg catggcttac    540
ccctccctgg cctctgagta ctctatccct gtgttcgaca acatgatgaa ccgccacctc    600
gtcgctcagg atctgttcag cgtgtacatg gaccgtaacg gtcaggagtc catgcttact    660
ctgggcgcca tcgatccctc ttactacacc ggttccctcc actgggttcc tgtgaccgtc    720
cagcagtact ggcagttcac cgtggacagc gtcactatct ccggcgtggt tgtggcttgc    780
gagggtggct gtcaggccat ccttgatact ggtaccagca agctcgtcgg cccctccagc    840
gacatcctga acatccagca ggctatcggt gccacccaga accagtacgg cgagttcgat    900
atcgactgcg ataaccttc ttacatgcct actgtggttt tcgagatcaa cggtaagatg    960
taccccctta ctccttctgc ttacacttcc caggatcagg gcttctgtac ctctggtttc   1020
cagtctgaga ccacagcca gaagtggatc cttggcgatg tcttcatccg cgagtactac   1080
tccgtcttcg accgtgccaa caacctggtg ggtctcgcta aggccatctg atcctctaga   1140
gt                                                                  1142
```

<210> SEQ ID NO 3
<211> LENGTH: 408
<212> TYPE: DNA
<213> ORGANISM: artificial
<220> FEATURE:
<223> OTHER INFORMATION: an approximately 410 bp SalI-SphII I fragment made using synthetic oligonucleotides (SEQ ID XXX-1)

<400> SEQUENCE: 3

```
cggtcgaccg ctacggtgac tgacacctgg cgtgccgaga tcactcgcat ccccctctac      60
aagggcaagt ctctgcgtaa ggctctcaag gagcacggtc tgctcgagga tttcctgcag     120
aagcagcagt acggcatcag ctctaagtac agcggtttcg gcgaggtggc cagcgtgcct     180
ctcactaact acctggacag ccagtacttc ggtaagatct accttggcac tcccctcag      240
gagttcaccg ttctgttcga tactggttcc agcgacttct gggttccctc catctactgt     300
aagagcaacc ttgcaagaa ccaccagcgc ttcgatcctc gcaagtccag caccttccag      360
aaccttggca agccccttc catccactac ggtactggca gcatgcag                   408
```

<210> SEQ ID NO 4
<211> LENGTH: 233
<212> TYPE: DNA
<213> ORGANISM: artificial
<220> FEATURE:
<223> OTHER INFORMATION: an approximately 220 bp SphI-BsrGI fragment made using synthetic oligonucleotides (SEQ ID XXX-2)

<400> SEQUENCE: 4

```
gcagcatgca gggtatcctt ggctacgaca ccgttaccgt gtccaacatc gtcgatattc      60
agcagaccgt gggtctgagc acccaggagc ctggcgatgt cttcacttac gccgagttcg     120
atggtatcct cggcatggct taccctccc tggcctctga gtactctatc cctgtgttcg      180
acaacatgat gaaccgccac ctcgtcgctc aggatctgtt cagcgtgtac atg           233
```

<210> SEQ ID NO 5
<211> LENGTH: 200
<212> TYPE: DNA
<213> ORGANISM: Artificial
<220> FEATURE:
<223> OTHER INFORMATION: an approximately 190 bp BsrGI-KpnI fragment made using synthetic oligonucleotides (SEQ ID XXX-3)

<400> SEQUENCE: 5

```
gcgtgtacat ggaccgtaac ggtcaggagt ccatgcttac tctgggcgcc atcgatccct      60
cttactacac cggttccctc cactgggttc ctgtgaccgt ccagcagtac tggcagttca     120
ccgtggacag cgtcactatc tccggcgtgg ttgtggcttg cgagggtggc tgtcaggcca     180
tccttgatac tggtaccagc                                                 200
```

<210> SEQ ID NO 6
<211> LENGTH: 334
<212> TYPE: DNA
<213> ORGANISM: artificial
<220> FEATURE:
<223> OTHER INFORMATION: an approximately 320 bp KpnI-XbaI fragment made using synthetic oligonucleotides (SEQ ID XXX-4)

<400> SEQUENCE: 6

```
ctggtaccag caagctcgtc ggcccctcca gcgacatcct gaacatccag caggctatcg      60
gtgccaccca gaaccagtac ggcgagttcg atatcgactg cgataacctt tcttacatgc     120
ctactgtggt tttcgagatc aacggtaaga tgtacccct tactccttct gcttacactt     180
cccaggatca gggcttctgt acctctggtt ccagtctga gaaccacagc cagaagtgga     240
tccttggcga tgtcttcatc cgcgagtact actccgtctt cgaccgtgcc aacaacctgg     300
tgggtctcgc taaggccatc tgatcctcta gagt                                 334
```

<210> SEQ ID NO 7
<211> LENGTH: 334
<212> TYPE: DNA
<213> ORGANISM: artificial
<220> FEATURE:
<223> OTHER INFORMATION: a modified KpnI-XbaI fragment designed for
      construction of the modBM gene (SEQ ID XXX-5).

<400> SEQUENCE: 7
ctggtaccag caagctcgtc ggcccctcca gcgacatcct gaacatccag caggctatcg      60
gtgccaccca gaaccagtac ggcgagttcg atatcgactg cgataacctt tcttacatgc     120
ctactgtggt tttcgagatc aacggtaaga tgtaccccct tactccttct gcttacactt     180
cccaggatca gggcttctgt acctctggtt tccagtctga gaaccacacc cagaagtgga     240
tccttggcga tgtcttcatc cgcgagtact actccgtctt cgaccgtgcc aacaacctgg     300
tgggtctcgc taaggccatc tgatcctcta gagt                                 334

<210> SEQ ID NO 8
<211> LENGTH: 66
<212> TYPE: DNA
<213> ORGANISM: artificial
<220> FEATURE:
<223> OTHER INFORMATION: synthetic polylinker
      (SalI-SphI-BsrGI-KpnI-XbaI) (SEQ ID XXX-6)

<400> SEQUENCE: 8
ggccaggcgc gccttccatg gaagaatgcg gccgctaaac catcgatggc tcgagttggc      60
gcgcca                                                                66

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 9
catgtacacg ctgaacagat cctgagc                                         27

<210> SEQ ID NO 10
<211> LENGTH: 74
<212> TYPE: DNA
<213> ORGANISM: Artificial Sequence
<220> FEATURE:
<223> OTHER INFORMATION: Description of Artificial Sequence:Primer

<400> SEQUENCE: 10
cgtcgaccgc tacggtgact gacacctggc gtaccgacaa ctccaccgag atcactcgca      60 tcccctcta caag                                                        74